US010677809B2

(12) United States Patent
Boehm et al.

(10) Patent No.: US 10,677,809 B2
(45) Date of Patent: Jun. 9, 2020

(54) ROTATABLE CARTRIDGE WITH MULTIPLE METERING CHAMBERS

(71) Applicant: Roche Diagnostics Operations, Inc., Indianapolis, IN (US)

(72) Inventors: Christoph Boehm, Viernheim (DE); Sascha Lutz, Neustadt (DE); Thomas Keller, Schifferstadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 223 days.

(21) Appl. No.: 15/807,802

(22) Filed: Nov. 9, 2017

(65) Prior Publication Data

US 2018/0136243 A1     May 17, 2018

(30) Foreign Application Priority Data

Nov. 16, 2016  (EP) .................................... 16199213

(51) Int. Cl.
*G01N 35/00* (2006.01)
*G01N 33/50* (2006.01)
(Continued)

(52) U.S. Cl.
CPC ...... *G01N 35/00584* (2013.01); *B01L 3/5027* (2013.01); *B01L 3/502753* (2013.01);
(Continued)

(58) Field of Classification Search
CPC ............. G01N 35/00584; G01N 35/00; G01N 33/5005; G01N 35/00069; G01N 35/1016;
(Continued)

(56) References Cited

U.S. PATENT DOCUMENTS 8,114,351 B2   2/2012  Degenhardt
8,470,588 B2   6/2013  Boehm et al.
(Continued)

FOREIGN PATENT DOCUMENTS

WO   WO-2014010927 A1 *  1/2014  ........ B01L 3/502753
WO      2015185763 A1   12/2015

OTHER PUBLICATIONS

Kim et al., "Flow-enhanced electrochemical immunosensors on centrifugal microfluidic platforms", Lab on a Chip, RSC Publishing;The Royal Society of Chemistry, 2013, 13, pp. 3747-3754.
(Continued)

*Primary Examiner* — Benjamin R Whatley
*Assistant Examiner* — Curtis A Thompson
(74) *Attorney, Agent, or Firm* — Dinsmore & Shohl, LLP

(57) ABSTRACT

A method and cartridge for determining an amount of at least two analytes in a biological sample and an automatic analyzer are disclosed. The cartridge may comprise a cartridge inlet, a sample holding chamber fluidically connected to the inlet, and two or more metering chambers. Each metering chamber may comprise a sample inlet, a sample outlet, and a metered outlet for dispensing a predetermined volume. At least one sample distribution channel is connected between the sample outlet of a metering chamber with a sample inlet of another metering chamber. For each metering chamber, a connecting tube fluidically connects the sample inlet with the sample holding chamber, a microfluidic structure for processing the sample into a processed sample connects to the sample outlet, and a measurement structure fluidically connects to the microfluidic structure and enables measurement of the processed sample to determine the amount of the analyte in the processed sample.

15 Claims, 11 Drawing Sheets

(51) Int. Cl.
  *B01L 3/00* (2006.01)
  *G01F 13/00* (2006.01)
  *G01N 35/10* (2006.01)
(52) U.S. Cl.
  CPC ........ *G01F 13/00* (2013.01); *G01N 33/5005* (2013.01); *G01N 35/00* (2013.01); *G01N 35/00069* (2013.01); *B01L 2200/0605* (2013.01); *B01L 2200/0621* (2013.01); *B01L 2200/10* (2013.01); *B01L 2300/0803* (2013.01); *B01L 2300/0806* (2013.01); *B01L 2300/087* (2013.01); *B01L 2300/0864* (2013.01); *B01L 2400/0409* (2013.01); *G01N 35/1016* (2013.01); *G01N 2035/00495* (2013.01)
(58) Field of Classification Search
  CPC ..... G01N 2035/00495; B01L 3/502753; B01L 3/5027; B01L 2400/0409; B01L 2300/0864; B01L 2300/0803; B01L 2200/0621; B01L 2200/0605; B01L 2200/10; B01L 2300/0806; B01L 2300/087; G01F 13/00
  See application file for complete search history.

(56) References Cited

U.S. PATENT DOCUMENTS

| | | |
|---|---|---|
| 2011/0195502 A1 | 8/2011 | Tsai |
| 2012/0028852 A1 | 2/2012 | Lee et al. |
| 2013/0004964 A1* | 1/2013 | Boehm ............ B01L 3/502753 435/7.4 |
| 2013/0236376 A1* | 9/2013 | Augstein ........... B01L 3/502723 422/506 |
| 2014/0287524 A1 | 9/2014 | Lee et al. |
| 2015/0321192 A1* | 11/2015 | Lee ................... B01L 3/502753 436/180 |
| 2016/0214108 A1* | 7/2016 | Solomon ........... B01L 3/502715 |

OTHER PUBLICATIONS

Martinez-Duarte et al., "The integration of 3D carbon-electrode dielectrophoresis on a CD-like centrifugal microfluidic platform", Lab on a Chip, The Royal10, 2010, pp. 1030-1043.

Extended European Search Report completed Apr. 21, 2017, pertaining to EP16199213.6 filed Nov. 16, 2016.

* cited by examiner

ROTATABLE CARTRIDGE WITH MULTIPLE METERING CHAMBERS

TECHNICAL FIELD

The below disclosure relates to analytical test devices for biological samples, and more particularly to the design and use of rotatable cartridges for performing a measurement of a biological sample.

BACKGROUND

Two classes of analysis systems are known in the field of medical analysis: wet analysis systems, and dry-chemical analysis systems. Wet analysis systems, which essentially operate using "wet reagents" (liquid reagents), perform an analysis via a number of required step such as, for example, providing a sample and a reagent into a reagent vessel, mixing the sample and reagent together in the reagent vessel, and measuring and analyzing the mixture for a measurement variable characteristic to provide a desired analytical result (analysis result). Such steps are often performed using technically complex, large, line-operated analysis instruments, which allow manifold movements of participating elements. This class of analysis system is typically used in large medical-analytic laboratories.

On the other hand, dry-chemical analysis systems operate using "dry reagents" which are typically integrated in a test element and implemented as a "test strip", for example. When these dry-chemical analysis systems are used, the liquid sample dissolves the reagents in the test element, and the reaction of sample and dissolved reagent results in a change of a measurement variable, which can be measured on the test element itself. Above all, optically analyzable (in particular colorimetric) analysis systems are typical in this class, in which the measurement variable is a color change or other optically measurable variable. Electrochemical systems are also typical in this class, in which an electrical measurement variable characteristic for the analysis, in particular an electrical current upon application of a defined voltage, can be measured in a measuring zone of the test element using electrodes provided in the measuring zone.

The analysis instruments of the dry-chemical analysis systems are usually compact, and some of them are portable and battery-operated. The systems are used for decentralized analysis, for example, at resident physicians, on the wards of the hospitals, and in so-called "home monitoring" during the monitoring of medical-analytic parameters by the patient himself (in particular blood glucose analysis by diabetics or coagulation status by warfarin patients).

In wet analysis systems, the high-performance analysis instruments allow the performance of more complex multi-step reaction sequences ("test protocols"). For example, immunochemical analyses often require a multistep reaction sequence, in which a "bound/free separation" (hereafter "b/f separation"), i.e., a separation of a bound phase and a free phase, is necessary. According to one test protocol, for example, the probe can first be transported through a porous solid matrix, which contains a specific binding reagent for the analyte. A marking reagent can subsequently be caused to flow through the porous matrix, to mark the bound analyte and allow its detection. To achieve precise analysis, a washing step must be performed, in which unbound marking reagent is completely removed. Numerous test protocols are known for determining manifold analytes, which differ in manifold ways, but which share the feature that they require complex handling having multiple reaction steps, in particular also a b/f separation possibly being necessary.

Test strips and similar analysis elements normally do not allow controlled multistep reaction sequences. Test elements similar to test strips are known, which allow further functions, such as the separation of red blood cells from whole blood, in addition to supplying reagents in dried form. However, they normally do not allow precise control of the time sequence of individual reaction steps. Wet-chemical laboratory systems offer these capabilities, but are too large, too costly, and too complex to handle for many applications.

To close these gaps, analysis systems have been suggested which operate using test elements which are implemented in such a manner that at least one externally controlled (i.e., using an element outside the test element itself) liquid transport step occurs therein ("controllable test elements"). The external control can be based on the application of pressure differences (overpressure or low-pressure) or on the change of force actions (e.g., change of the action direction of gravity by attitude change of the test element or by acceleration forces). The external control is especially frequently performed by centrifugal forces, which act on a rotating test element as a function of the velocity of the rotation.

Analysis systems having controllable test elements are known and typically have a housing, which comprises a dimensionally-stable plastic material, and a sample analysis channel enclosed by the housing, which often comprises a sequence of multiple channel sections and chambers expanded in comparison to the channel sections lying between them. The structure of the sample analysis channel having its channel sections and chambers is defined by profiling of the plastic parts. This profiling is able to be generated by injection molding techniques or hot stamping. Microstructures, which are generated by lithography methods, increasingly being used more recently, however.

Analysis systems having controllable test elements allow the miniaturization of tests which have only been able to be performed using large laboratory systems. In addition, they allow the parallelization of procedures by repeated application of identical structures for the parallel processing of similar analyses from one sample and/or identical analyses from different samples. It is a further advantage that the test elements can typically be produced using established production methods and that they can also be measured and analyzed using known analysis methods. Known methods and products can also be employed in the chemical and biochemical components of such test elements.

In spite of these advantages, there is a further need for improvement. In particular, analysis systems which operate using controllable test elements are still too large. The most compact dimensions possible are of great practical significance for many intended applications.

U.S. Pat. No. 8,114,351 B2 discloses an analysis system for the analysis of a body fluid sample for an analyte. The analysis system provides a test element and an analysis instrument having a dosing station and a measurement station. The test element has a housing an (at least) one sample analysis channel enclosed by the housing. The test element is rotatable around an axis of rotation which extends through the test element.

U.S. Pat. No. 8,470,588 B2 discloses a test element and a method for detecting an analyte. The test element is essentially disk shaped and flat, and can be rotated about a preferably central axis which is perpendicular to the plane of the disk shaped test element.

Kim, Tae-Hyeong, et al. "Flow-enhanced electrochemical immunosensors on centrifugal microfluidic platforms." Lab on a Chip 13.18 (2013): 3747-3754, doi:10.1039/c3lc50374g, (hereafter "Kim et. al.") discloses a fully integrated centrifugal microfluidic device with features for target antigen capture from biological samples, via a bead-based enzyme-linked immune-sorbent assay, and flow-enhanced electrochemical detection. This is integrated into a Centrifugal microfluidic discs, also known as "lab-on-a-disc" or microfluidic CDs.

Martinez-Duarte, Rodrigo, et al. "The integration of 3D carbon-electrode dielectrophoresis on a CD-like centrifugal microfluidic platform." Lab on a Chip 10.8 (2010): 1030-1043, doi:10.1039/B925456K, (hereafter "Martinez-Duarte et. al.") discloses a dielectrophoresis (DEP)-assisted filter with a compact disk (CD)-based centrifugal platform. 3D carbon electrodes are fabricated using the C-MEMS technique and are used to implement a DEP-enabled active filter to trap particles of interest.

SUMMARY

Various embodiment disclosed hereinafter describe a method, a cartridge and an automatic analyzer.

For example, in an embodiment, a method of determining an amount of at least two analytes in a biological sample using a cartridge, wherein the biological sample comprises a fluid, and wherein the cartridge is operable for being spun around a rotational axis is disclosed. The cartridge may comprise: a cartridge inlet for receiving the biological sample; a sample holding chamber fluidically connected to the cartridge inlet; two or more metering chambers for receiving a predetermined volume of the biological sample, wherein each of the two or more metering chambers comprises a sample inlet, wherein each of the two or more metering chambers comprises a sample outlet, wherein each of the two or more metering chambers comprises a metered outlet for dispensing a predetermined volume; a connecting tube for each of the two or more metering chambers that fluidically connects the sample inlet with the sample holding chamber; at least one sample distribution channel, wherein each of the at least one sample distribution channel connects the sample outlet of a first selected metering chamber with a sample inlet of a second selected metering chamber, wherein the two or more metering chambers comprises the first selected metering chamber, wherein the two or more metering chambers comprise the second selected metering chamber, wherein the second selected metering chamber is adjacent to the first selected metering chamber; a microfluidic structure for each of the two or more metering chambers, wherein the microfluidic structure is connected to the metered outlet, wherein the microfluidic structure is configured for processing the biological sample into a processed sample; a measurement structure for each of the two or more metering chambers for enabling measurement of the processed sample to determine a concentration of the analyte in the processed sample, wherein the measurement structure is fluidically connected to the microfluidic structure. The method may comprise placing the biological sample into the cartridge inlet to at least partially fill the sample holding chamber; rotating the cartridge about the rotational axis to transport a portion of the sample from the sample holding chamber to each of the two or more metering chambers, wherein rotation of the cartridge causes simultaneous transport of a first part of the portion of the sample to each of the two or more metering chambers via the connecting tube for each of the two or more metering chambers, wherein rotation of the cartridge causes transport of a second part of the portion of the sample to at least one of the two or more metering chambers in serial via the at least one sample distribution channel; controlling the rotation of the cartridge about the rotational axis to transport a metered biological sample from each of the two or more metering chambers to the microfluidic structure, wherein the metered biological sample has the predetermined volume; controlling the rotation of the cartridge about the rotational axis to process the metered biological sample into the processed sample; controlling the rotation of the cartridge to transfer the processed sample from the microfluidic structure to the measurement structure; and measuring the amount of at least two analytes using the measurement structure of each of the two or more metering chambers and a measurement system.

In another embodiment, a cartridge for determining an amount of at least two analytes in a biological sample, wherein the cartridge is operable for being spun around a rotational axis, is disclosed. The cartridge may comprise a cartridge inlet for receiving the biological sample; a sample holding chamber fluidically connected to the cartridge inlet; two or more metering chambers for the biological sample for receiving a predetermine volume of the biological sample, wherein each of the two or more metering chambers comprises a sample inlet, wherein each of the two or more metering chambers comprises a sample outlet, wherein each of the two or more metering chambers comprises a metered outlet for dispensing a predetermined volume; a connecting tube for each of the two or more metering chambers that fluidically connects the sample inlet with the sample holding chamber; at least one sample distribution channel, wherein each of the at least one sample distribution chamber connects the sample outlet of a first selected metering chamber with a sample inlet of a second selected metering chamber, wherein the two or more metering chambers comprises the first selected metering chamber, wherein the two or more metering chambers comprise the second selected metering chamber, wherein the second selected metering chamber is adjacent to the first selected metering chamber; a microfluidic structure for each of the two or more metering chambers, wherein the microfluidic structure is connected to the metered outlet, wherein the microfluidic structure is configured for processing sample into a processed sample; and a measurement structure for each of the two or more metering chambers for enabling measurement of the processed sample to determine the amount of the analyte in the processed sample, wherein the measurement structure is fluidically connected to the microfluidic structure.

In still another embodiment, an automatic analyzer is disclosed which may comprise a cartridge according to any of the herein disclosed embodiments, and wherein the automatic analyzer may further comprise a cartridge spinner for controlling rotation of the cartridge about the rotational axis, and wherein the automatic analyzer further comprises a measurement system for measuring the amount of the at least two analytes using the measurement structure of each of the two or more metering chambers.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, and in which:

LIST OF REFERENCE NUMERALS

Figure 1:
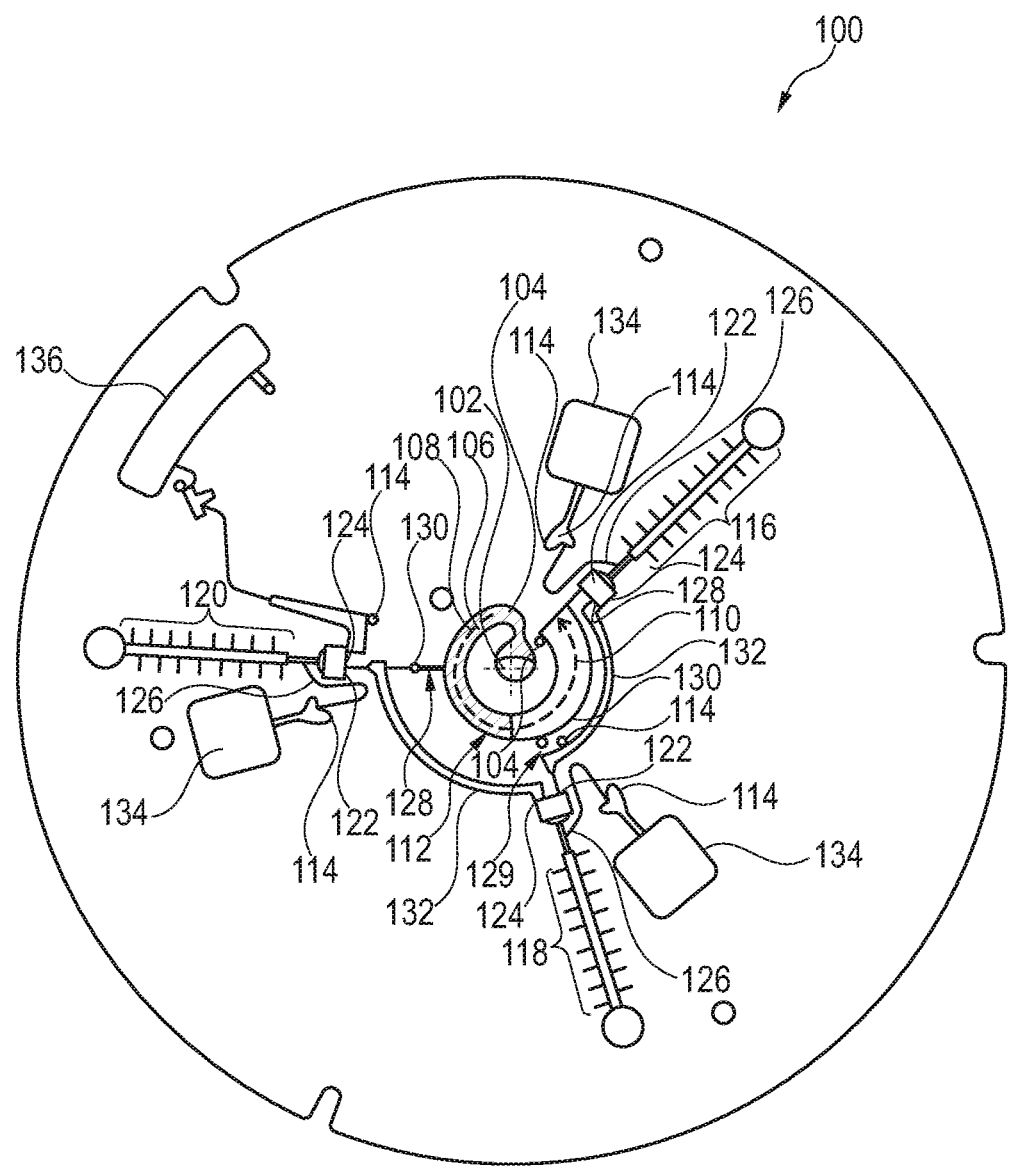
FIG. 1 illustrates an example of a cartridge.

100 cartridge
102 rotational axis
104 cartridge inlet
106 sample holding chamber
108 biological sample
110 elongated path
112 furthest edge
114 vent
116 first -metering chamber
118 second -metering chamber
120 last metering chamber
122 sample inlet
124 sample outlet
126 metered outlet
128 connecting tube
130 capillary stop
132 sample distribution channel
134 fluidic element
136 waste reservoir
200 sample bypass channel
800 microfluidic structure
802 reagent chamber
804 measurement structure
806 chromatographic membrane
808 waste fleece
810 detection window
812 blister with washing buffer
814 aliquoting structure
1000 automatic analyzer
1002 cartridge spinner
1004 motor
1006 gripper
1008 portion of cartridge
1010 measurement structure
1012 measurement system
1014 controller
1016 hardware interface
1018 processor
1020 electronic storage
1022 electronic memory
1024 network interface
1026 network connection
1028 laboratory information system
1030 executable instructions
1032 measurement Like numbered elements in these figures are either equivalent elements or perform the same function. Elements which have been discussed previously will not necessarily be discussed in later figures if the function is equivalent.

DETAILED DESCRIPTION

The use of rotational cartridges with fluidic structures to perform tests on biological samples can provide for cartridge and automatic analyzer systems that can be distributed to such places as clinics or doctors' offices. They may provide a very convenient and accurate way of providing diagnostic results inexpensively and quickly. A difficulty is that often times doctors or other caregivers may be interested in obtaining multiple test results. This can mean that a comparatively large volume of a biological sample needs to be obtained in order to have enough of the biological sample to place in to multiple cartridges.

It is not at all easy to divide a biological sample into multiple portions to have independent tests on the same cartridge. A major issue is that many biological samples have multiple components. For example a whole blood sample may comprise blood plasma, erythrocytes, and lipids. The act of dividing a whole blood sample into multiple portions for different diagnostic tests can have the effect of changing the ratio of plasma, erythrocytes, and lipids within the multiple portions. This can result in skewed or inaccurate test results.

Empirical tests of rotational cartridges showed that feeding multiple metering chambers simultaneously with whole blood results in inaccurate test results. Other test structures were also tried. Experiments were also performed where a series of metering chambers were filled sequentially. As the disk was rotated the whole blood was first forced into a first metering chamber. Sample distribution channels were used to connect the metering chambers sequentially or serially. This then caused the metering chambers to fill one after the other. These test cartridges also provided skewed or inaccurate test results. The relative ratio of the blood plasma, the erythrocytes and lipids was wrong. The multiple tests were inconsistent with each other.

Various embodiments disclosed herein may provide for a means of dividing a biological sample into multiple portions while maintaining its original composition closely enough so that accurate tests can be performed on each of the samples. Example cartridges do this by providing two separate pathways for filling the metering chambers with the biological sample. Embodiments have a holding chamber which initially stores the biological sample. Individual metering chambers are distributed about or around the holding chamber. There is a connecting tube for each of the metering chambers that is connected between the holding chamber and an inlet of the respective metering chamber. The metering chambers each have a sample inlet and outlet. The metering chambers are connected by a series of sample distribution channels. The sample distribution channels are connected from the outlet of one metering chamber to the inlet of an adjacent metering chamber. The sample distribution channels cause the metering chambers to fill serially or one after the other.

The connecting tubes provide a parallel or simultaneous filling pathway for the metering chambers, and the distribution channels form a sequential filling pathway for the metering chamber. When the cartridge is rotated about its rotational axis the biological sample is then forced through the connecting tubes and each of the metering chambers begins to fill. As metering chambers begin to be filled completely the excess is routed through a distribution channel to a neighboring or adjacent metering chamber. The effect of using both means of filling the metering chambers is that biological sample in the metering chambers more closely resembles the composition of the biological sample that was originally placed in the sample holding chamber.

The above described structure was tested with whole blood. The effect is also valid for other biological samples such as semen, a stool sample mixed with fluid, or other fluids which have multiple components. It is also beneficial to use with biological samples that are not normally considered to have multiple components, because a biological sample can be contaminated. For example urine could be contaminated with cells or even calcium crystals. Use of the cartridges described herein may provide for a test structure that provides for more accurate, uniform, and robust results when the original biological sample is divided into multiple sub samples using two or more metering chambers.

A cartridge as used here encompasses also any test element for processing the biological sample into a processed biological sample. The cartridge may include structures or components which enable a measurement to be performed on the biological sample. A cartridge is a test element as is defined and explained in U.S. Pat. Nos. 8,114,351 B2 and 8,470,588 B2. A cartridge as used herein may also be referred to as a Centrifugal microfluidic disc, also known as "lab-on-a-disc" or a microfluidic CD.

It is understood that references to biological samples and products below and in the claims may be modified such that they refer to blood samples and/or blood products and/or whole blood.

A biological sample as used herein encompasses a chemical product derived, copied, replicated, or reproduced from a sample taken from an organism.

In one embodiment, a method of determining an amount of at least two analytes in a biological sample using a cartridge is disclosed. The biological sample comprises a fluid. The cartridge is operable for being spun around a rotational axis.

In another embodiment, a method of determining an amount of one analyte at least two times (to increase the precision of the analysis) in a biological sample using a cartridge is also disclosed.

The cartridge may comprise a cartridge inlet for receiving the biological sample. The cartridge may further comprise a sample holding chamber connected to the cartridge inlet. The cartridge may further comprise two or more metering chambers for receiving a predetermined volume of the biological sample. Each of the two or more metering chambers comprises a sample inlet. Each of the two or more metering chambers comprises a sample outlet. Each of the two or more metering chambers comprises an outlet for a metered sample volume. The metered sample volume is a portion of the predetermined volume of the biological sample that goes into each of the metering chambers.

The cartridge may further comprise a connecting tube for each of the two or more metering chambers that fluidically connect the sample inlet with the sample holding chamber. The cartridge may further comprise at least one sample distribution channel. Each of the at least one sample distribution channel is connected between the sample outlet of a first selected metering chamber with the sample inlet of a second selected metering chamber. The two or more metering chambers comprise the first selected metering chamber. The two or more metering chambers comprise the second selected metering chamber. The second selected metering chamber is adjacent to the first selected metering chamber.

The connecting tube connects the individual metering chambers directly with the sample holding chamber. The sample distribution channels are configured to serially connect the metering chambers. This provides two distinct routes for the biological sample to flow into each of the two or more metering chambers.

The cartridge may further comprise a microfluidic structure for each of the two or more metering chambers. The microfluidic structure is connected to the sample outlet. The microfluidic structure is configured for processing the metering sample volume into a processed sample. The cartridge may further comprise a measurement structure for each of the two or more metering chambers for enabling measurement of the processed sample to determine a concentration of the analyte in the processed sample. The concentration of the analyte is directly related to the concentration of the analyte in the biological sample. The measurement structure is fluidically connected to the microfluidic structure.

The measurement structure may take different forms in different examples. For example in one example the measurement structure may be a chromatographic membrane with antibodies that attach to markers in the processed sample. Fluorescent markers may then be used to perform the measurement of the amount of the analyte. In other examples, the processed sample may be transported to an optically transparent container or region which may then be subjected to spectrographic measurements.

In other embodiments, the method comprises placing the biological sample into the cartridge inlet to at least partially fill the sample holding chamber. The method further comprises rotating the cartridge about the rotational axis to transport a portion of the sample from the sample holding chamber to each of the two or more metering chambers. Rotation of the cartridge causes simultaneous transport of a first part of the portion of the sample to each of the two or more metering chambers via the connecting tube for each of the two or more metering chambers. Rotation of the cartridge further causes transport of a second part of the portion of the sample to each of the two or more metering chambers in serial via the at least one sample distribution channel. The simultaneous transfer of fluid via two different routes to the two or more metering chambers may be beneficial because the composition of the predetermined volume of the biological sample may have a composition or makeup that is closer to the biological sample if only one of the two routes is used. For example multi-component biological samples such as whole blood contain essentially a solid such as whole blood cells, blood plasma and also lipids. The use of the multiple ways of filling the two or more metering chambers may provide for better results. The method further comprises controlling the rotation of the cartridge about the rotational axis to transport the metered sample from each of the two or more metering chambers to the microfluidic structure. The method may further comprise controlling the rotation of the cartridge about the rotational axis to process the sample into the processed sample. The method may further comprise controlling the rotation of the cartridge to transfer the processed sample from the microfluidic structure of each of the two or more metering chambers to the measurement structure. The method may further comprise measuring the amount of the at least two analytes using the measurement structure of each of the two or more metering chambers and a measurement system. The measurement may include, but is not limited to: a photometric transmission measurement, a measurement of the scattering of light, a chemiluminescence, a fluorescence measurement, an electrochemical and electrochemiluminescense (ECL) measurement.

The above described embodiments may be beneficial because providing multiple routes for the biological sample to the two or more metering chambers may provide more accurate measurement of the amount of the at least two analytes.

In another embodiment the cartridge inlet is located closer to the rotational axis than the sample holding chamber. The sample holding chamber is elongated along an elongated path. The elongated path is at least partially encircling the rotational axis. The sample holding chamber has a furthest edge from the rotational axis. The distance from the furthest edge to the rotational axis increases along the elongated path. The connecting tube for each of the two or more metering chambers is connected to the sample holding chamber at the furthest edge. This embodiment may be beneficial because the structure of the sample holding chamber may force blood through each of the connecting tubes into the two or more metering chambers individually.

In another embodiment the biological sample is a multi-component fluid. A multi-component fluid as used herein encompasses a fluid that is mixed any one of the following: with a solid or sediment, a second fluid, biological cells, a colloidal suspension, an oil, a lipid, blood serum, and combinations thereof.

In another embodiment, a cartridge for determining an amount of at least two analytes in a biological sample is disclosed. The cartridge is operable for being spun around a rotational axis. The cartridge comprises a cartridge inlet for receiving the biological sample. The cartridge further comprises a sample holding chamber connected to the cartridge inlet. The cartridge further comprises two or more metering chambers for the biological sample for receiving a predetermined volume of the biological sample. Each of the two or more metering chambers comprises a sample inlet. Each of the two or more metering chambers comprises a metered outlet. The cartridge further comprises a connecting tube for each of the two or more metering chambers that fluidically connect the sample inlet with the sample holding chamber. The cartridge further comprises at least one sample distribution chamber.

Each of the at least one sample distribution chamber is connected with the sample outlet of a first selected metering chamber with a sample inlet and a second selected metering chamber. The two or more metering chambers comprise the first selected metering chamber. The two or more metering chambers comprise the second selected metering chamber. The second selected metering chamber is adjacent to the first selected metering chamber. The cartridge further comprises a microfluidic structure for each of the two or more metering chambers. The microfluidic structure is connected to the sample outlet. The microfluidic structure is configured for processing the biological sample into a processed sample. The cartridge further comprises a measurement structure for each of the two or more metering chambers for enabling measurement of the processed sample to determine the amount of the analyte in the sample. The measurement structure is fluidically connected to the microfluidic structure.

In another embodiment the two or more metering chambers comprise a first filled metering chamber and one or more sequentially filled metering chambers. The term first filled metering chamber is a label which is used to refer to one of the metering chambers. Each of the one or more sequentially filled metering chambers comprises a sample bypass channel that fluidically connects the sample inlet with the sample outlet. The use of the sample bypass channel may be beneficial because it may enable the cartridge to distribute the biological sample to each of the two or more metering chambers when the sample holding chamber is overfilled.

In another embodiment the two analytes each comprise any one of the following: Troponin T, Troponin I, CKMB, NTproBNP, D-Dimer, Myoglobin, Thyroid-stimulating hormone (TSH) and Procalcitonin (PCT).

In another embodiment the cartridge is formed from a plastic disc and a cover plate. At least a portion of the sample chamber is visible through the cover plate and/or the plastic disc. Making the portion of the sample chamber visible may be useful in aiding an operator of the cartridge in seeing when the sample chamber is properly filled.

In another embodiment the sample holding chamber is configured for receiving the sample with a volume between 30 µl and 500 µl. The broad range may be beneficial because it is not necessary for the user of the cartridge to accurately measure the biological sample before placing it into the cartridge inlet.

In another embodiment each of the measurement structures is a chromatographic membrane.

In another embodiment the measurement structure comprises a waste fleece or absorbent zone.

The chromatographic membrane may be referred to as a capillary-active zone. In one embodiment, the capillary-active zone comprises a porous, absorbent matrix. In one embodiment of the test element, the second end of the capillary-active zone near to the axis adjoins a further absorbent material or an absorbent structure such that it can take up liquid from the capillary-active zone. The capillary-active zone and the further absorbent material typically slightly overlap for this purpose. The further material or the further absorbent structure serve on the one hand, to assist the suction action of the capillary-active zone and in particular of the porous, absorbent matrix and, on the other hand, serve as a holding zone for liquid which has already passed through the capillary-active zone. In this connection the further material can consist of the same materials or different materials than the matrix. For example, the matrix can be a membrane and the further absorbent material can be a fleece or a paper. Other combinations are of course equally possible.

The fluidic structure may contain a reagent zone which contains a conjugate of an analyte binding partner (typically an antibody or an immunologically active antibody fragment capable of analyte binding if the analyte is an antigen or hapten, or an antigen or hapten if the analyte is an antibody) and a label which can be detected directly or indirectly by visual, optical or electrochemical means, wherein the conjugate can be dissolved by the liquid sample. Suitable labels are, for example, enzymes, fluorescent labels, chemiluminescent labels, electrochemically active groups or so-called direct labels such as metal or carbon labels or colored lattices. This zone may also be referred to as the conjugate zone.

The conjugate zone can serve also as a sample application zone or a separate sample application zone can be located on the test element. The conjugate zone can, in addition to the conjugate of analyte binding partner and label described above, also contain an additional conjugate of a second analyte binding partner (which is in turn typically an antibody or an immunologically active antibody fragment capable of analyte binding) and a tagging substance which is itself a partner in a binding pair. The tagging substance can for example be biotin, streptavidin or digoxigenin and can be used to immobilize a sandwich complex consisting of labelled conjugate, analyte and tagged conjugate in the detection and/or control zone.

The chromatographic membrane may additionally comprise a detection zone which contains a permanently immobilized binding partner (i.e., one that cannot be detached by the liquid sample) for the analyte or for complexes containing the analyte. The immobilized binding partner is in turn typically an antibody or an immunologically active antibody fragment capable of analyte binding or an antigen or (poly) hapten. If one of the above-mentioned tagged conjugates is used which for example comprises biotin or digoxigenin together with an analyte binding partner, the immobilized binding partner can also be streptavidin or polystreptavidin and an anti-digoxigenin antibody.

Finally, there may also be a control zone in or on the chromatographic membrane which contains a permanently immobilized binding partner for the conjugate of analyte binding partner and label for example in the form of an immobilized polyhapten which acts as an analyte analogue and is able to bind the analyte binding partner from the labeled conjugate. The control zone may additionally contain one or more permanently immobilized binding partner(s) for the analyte or for complexes containing the analyte. The latter binding partners can be selected from the same compounds which were described above in connection with the immobilized binding partners of the detection zone. These immobilized binding partners in the detection zone and in the control zone are typically identical. They may, however, also be different for example in that a binding partner for a biotin-tagged conjugate (hence, e.g., polystreptavidin) is immobilized in the detection zone and an anti-analyte antibody is immobilized in the control zone in addition to the polyhapten. In the latter case the anti-analyte antibody that is additionally immobilized in the control zone should be directed against (another) independent epitope and thus one that is not recognized by the conjugate antibodies (biotin-tagged conjugate and labelled conjugate).

In another embodiment, the absorbent structure is a waste fleece.

In another embodiment, the chromatographic membrane can contain one or more zones containing immobilized reagents.

Specific binding reagents for example specific binding partners such as antigens, antibodies, (poly) haptens, streptavidin, biotin, polystreptavidin, ligands, receptors, nucleic acid strands (capture probes) are typically immobilized in the capillary-active zone and in particular in the porous, absorbent matrix. They are used to specifically capture the analyte or species derived from the analyte or related to the analyte from the sample flowing through the capillary-active zone. These binding partners can be present immobilized in or on the material of the capillary-active zone in the form of lines, points, patterns or they can be indirectly bound to the capillary-active zone e.g., by means of so-called beads. Thus, for example, in the case of immunoassays one antibody against the analyte can be present immobilized on the surface of the capillary-active zone or in the porous, absorbent matrix which then captures the analyte (in this case an antigen or hapten) from the sample and also immobilizes it in the capillary-active zone such as, e.g., the absorbent matrix. In this case the analyte can be made detectable for example by means of a label that can be detected visually, optically or fluorescence-optically by further reactions, for example by additionally contacting it with a labelled bindable partner.

In another embodiment, the fluidic structure contains a first specific binding partner of the analyte with a detectable label and a second specific binding partner with a capture label. These both form a binding complex with the analyte. This may consist of a first specific binding partner, a second specific binding partner and an analyte. This may additionally provide for a measurement structure within the immobilized binding partner specific to the capture label of the second specific binding partner.

In another embodiment, the detection is fluorescence-based.

In another embodiment, the label is particle-based fluorescent label.

In another embodiment, the chromatographic membrane contains an optical calibration zone. The optical calibration zone may for example be a region on the measurement structure which contains a defined amount of the immobilized label and provides a means for checking if the optics of the instrument is functioning properly and if not, to calibrate it adequately. In other embodiments, the optical calibration zone is located at different locations on the test element.

In another embodiment, the measurement structure contains a reagent and flow control zone. This may provide for a means of checking if the cartridge is functioning properly in terms of reagents and immunochromatography. There may be for example two different control zones, a reagent/flow-control and an optical calibration zone as instrument control zone for correcting the intensity of the radiation or excitation source when an optical measurement is made.

In another embodiment, the cartridge is disk-shaped or at least partially disk-shaped.

In another embodiment, the cartridge may have an outer edge which fits within a circle drawn around the rotational axis.

In another embodiment, the cartridge has an outer edge. The outer edge may have a portion or portions that are circularly symmetric around the rotational axis.

In another embodiment the two or more metering chambers are any one of the following: three metering chambers, four metering chambers, and five metering chambers.

In another embodiment the two or more metering chambers comprises a last filled metering chamber. The term last filled metering chamber is a label for a particular metering chamber. The cartridge further comprises a waste reservoir connected to the sample outlet of the metering chamber. When the two or more metering chambers are filled sequentially the last filled metering chamber is the one that is furthest on the chain of the sample distribution channels.

In another embodiment the cartridge inlet is located closer to the rotational axis than the sample holding chamber. The sample holding chamber is elongated along an elongated path. The elongated path is at least partially encircling the rotational axis. The sample holding chamber has a furthest edge from the rotational axis. The distance from the furthest edge to the rotational axis increases along the elongated path. The connecting tube for each of the two or more metering chambers is connected to the sample holding chamber at the furthest edge.

In another embodiment the connecting tube of each of the two or more metering chambers further connects to one of the at least one sample distribution channel adjacent to the sample inlet. This may be beneficial because it provides a common place for the biological sample to enter the metering chamber.

In another embodiment the connecting tube of each of the two or more metering chambers comprises a capillary stop. The use of the capillary stop may be beneficial because the fluid in the sample holding chamber does not flow or move into the two or more metering chambers until a rotation of the cartridge about the rotational axis begins. This may be beneficial in controlling the flow of the biological sample into the two or more metering chambers.

In another embodiment the biological sample is any one of the following: whole blood, urine, semen, saliva, a stool sample mixed with a liquid, blood plasma, blood serum and interstitial fluid.

In another embodiment the measurement structure comprises two or more electrodes and/or an optical measurement structure. The measurement system comprises a system for making an electrical measurement. The measurement system comprises a system for making optical measurements.

In some embodiments the optical measurement structure may be a transparent structure or an optically transparent structure. The measurement system comprises an optical measurement system.

In some examples optically transparent may include near infrared and near ultraviolet. In other examples optically transparent may exclude the near infrared or near ultraviolet.

Some examples may have both the measurement structure with the transparent structure and also the electrodes for more complicated tests. For example the measurement structure may be a structure for making electrochemiluminescence measurements where electrodes cause an optical excitation in a sample.

In other examples the measurement structure comprises two or more electrodes for making an electrical measurement or ECL measurement of the processed biological sample. For example the measurement structures of Martinez-Duarte et al. or Kim et al. may be incorporated into a cartridge.

Examples may also only have electrode. For example in an electrochemical detection structure an electrode may be used to measure a current caused by the result of an enzymatic reaction.

In another aspect, the automatic analyzer further comprises a cartridge spinner for controlling the rotation of the cartridge about the rotational axis. The automatic analyzer further comprises a measurement system for measuring the amount of the at least two analytes using the measurement structure of each of the two or more metering chambers.

The automatic analyzer further comprises a memory for storing machine-executable instructions and a processor for controlling the automatic analyzer. Execution of the machine-executable instructions further cause the processor to control the cartridge spinner to rotate the cartridge about the rotational axis to transport a portion of a biological sample from the sample holding chamber to each of the two or more metering chambers. Rotation of the cartridge causes simultaneous transport of a first part of the portion of the biological sample to each of the two or more metering chambers via the connecting tubes for each of the two or more metering chambers. Rotation of the cartridge causes transport of a second part of the portion of the biological sample to each of the two or more metering chambers in serial via the at least one blood distribution channel.

Execution of the machine-executable instructions further causes the processor to control the cartridge spinner to control the rotation of the cartridge about the rotational axis to transport a metered sample from each of the two or more metering chambers to the microfluidic structure. Execution of the machine-executable instructions further cause the processor to control the cartridge spinner to control the rotation of the cartridge about the rotational axis to process the metered sample into a processed sample. Execution of the machine-executable instructions further cause the processor to control the cartridge spinner to control the rotation of the cartridge to transfer the processed sample from the microfluidic structure of each of the two or more metering chambers to the measurement structure. Execution of the machine-executable instructions further cause the processor to measure the amount of at least two analytes using the measurement structure of each of the two or more metering chambers and a measurement system.

In another embodiment the biological sample is a whole blood sample. The two or more metering chambers are two or more plasma separation chambers. The plasma separation chamber may also be referred to as a blood separation chamber. The United States Patent US 2009/0191643 A1 illustrates a microfluidic structure in a rotational disc that is able to separate serum or plasma from the blood cell fraction (mainly the erythrocytes) of a whole blood sample.

Execution of the machine-executable instructions further cause the processor to control the cartridge spinner to control the rotation of the cartridge about the rotational axis to separate blood plasma from the portion of the whole blood sample in each of the two or more plasma separation chambers by centrifugation.

It is understood that one or more of the aforementioned embodiments may be combined as long as the combined embodiments are not mutually exclusive. Refers is now made hereafter to the various illustrated embodiments of the figures.

FIG. 1 shows an example of a cartridge. The cartridge 100 has a rotational axis 102. The cartridge also comprises a cartridge inlet 104. In this example the cartridge inlet 104 is located where the rotational axis 102 is. However, the cartridge inlet 104 could also be off of the rotational axis 102. The cartridge inlet 104 is connected to a sample holding chamber 106. In this example the sample holding chamber 106 follows an elongated path 110. The elongated path partially wraps around the rotational axis 102. The sample holding chamber 106 has a furthest edge 112 that is the edge furthest from the rotational axis 102.

The sample holding chamber 106 in FIG. 1 can be seen as containing a biological sample 108 that has been placed into the sample holding chamber 106. Within various structures of the cartridge 100 there can be seen a number of vents 114. The cartridge 100 further comprises a first metering chamber 116, a second metering chamber 118, and a last metering chamber 120. Each metering chamber 116, 118, 120 has a sample inlet 122, a sample outlet 124, and a metered outlet 126. There is a connecting tube 128 for each of the metering chambers 116, 118, 120 that connect directly from the sample inlet 122 to the furthest edge 112 of the sample holding chamber 106. Fluid can travel directly from the sample holding chamber 106 to the sample inlets 122.

In FIG. 1 there are also two sample distribution channels 132 that are shown. The sample distribution channels 132 are used to also sequentially fill the metering chambers 116, 118, 120. One of the sample distribution channels 132 connects the sample outlet 124 of the first metering chamber 116 to the sample inlet 122 of the second metering chamber 118. There is a second sample distribution channel 132 connected to the sample outlet 124 of the second metering chamber 118 and connected to the sample inlet 122 of the last metering chamber 120. The combination of the connecting tubes 128 and the sample distribution channels 132 cause the metering chambers 116, 118, 120 to be filled both in serial and in parallel. This method of filling may be particularly beneficial when the biological sample comprises multiple components.

For example if the biological sample 108 contains a solid such as red blood cells, as it spins it may cause the red blood cells to concentrate in the first metering chamber 116. Also using as an example, whole blood also contains fatty components such as lipids. When performing multiple tasks using a single sample it is beneficial if the original biological sample has a composition in the metering chambers 116, 118, 120 that is as close as possible to the composition of the biological sample 108. The use of both the connecting tubes 128 to fill in parallel and the sample distribution channels 132 to fill in serial have been shown experimentally to provide samples in the metering chambers 116, 118, 120 that match the composition of the biological sample 108 more closely than if the filling of the metering chambers 116, 118, 120 is performed using serial or parallel filling alone. When parallel filling is used alone the problem is not the composition of the multiple samples, but the difficulty in the equal distribution of the volumes of each of the samples. With parallel filling alone, it is difficult to ensure that each metering structure is filled completely.

Each of the metering chambers 116, 118, 120 comprises a metered output 126 that is connected to a fluidic element. Each fluidic element 134 depicted in FIG. 1 was a test element used to simulate a microfluidic structure and a measurement structure on a test disc. The fluidic elements 134 may be used to collect the metered biological sample. The fluidic elements 134 may be easily replaced with other structures such as a microfluidic structure for processing the metered sample into a processed sample and also a measurement structure. Such structures are shown in some later figures.

The cartridge 100 is shown as optionally containing a waste reservoir 136 which is connected to the sample outlet 124 of the last metering chamber 120.

FIGS. 2-7 illustrate the distribution of a biological sample into three metering chambers. The cartridge 100 illustrated in FIGS. 2-7 is identical to the cartridge 100 in FIG. 1 except with the addition of sample bypass channels 200 that connect the sample inlet 122 to the sample outlet 124 of the second metering chamber 118 and the last metering chamber 120. In experiments the addition of the sample bypass channel 200 has been shown to be effective in preserving the composition of the biological sample 108 when it is distributed to the filled metering chambers 116, 118, 120 when the sample holding chamber 106 is overfilled.

Figure 2:
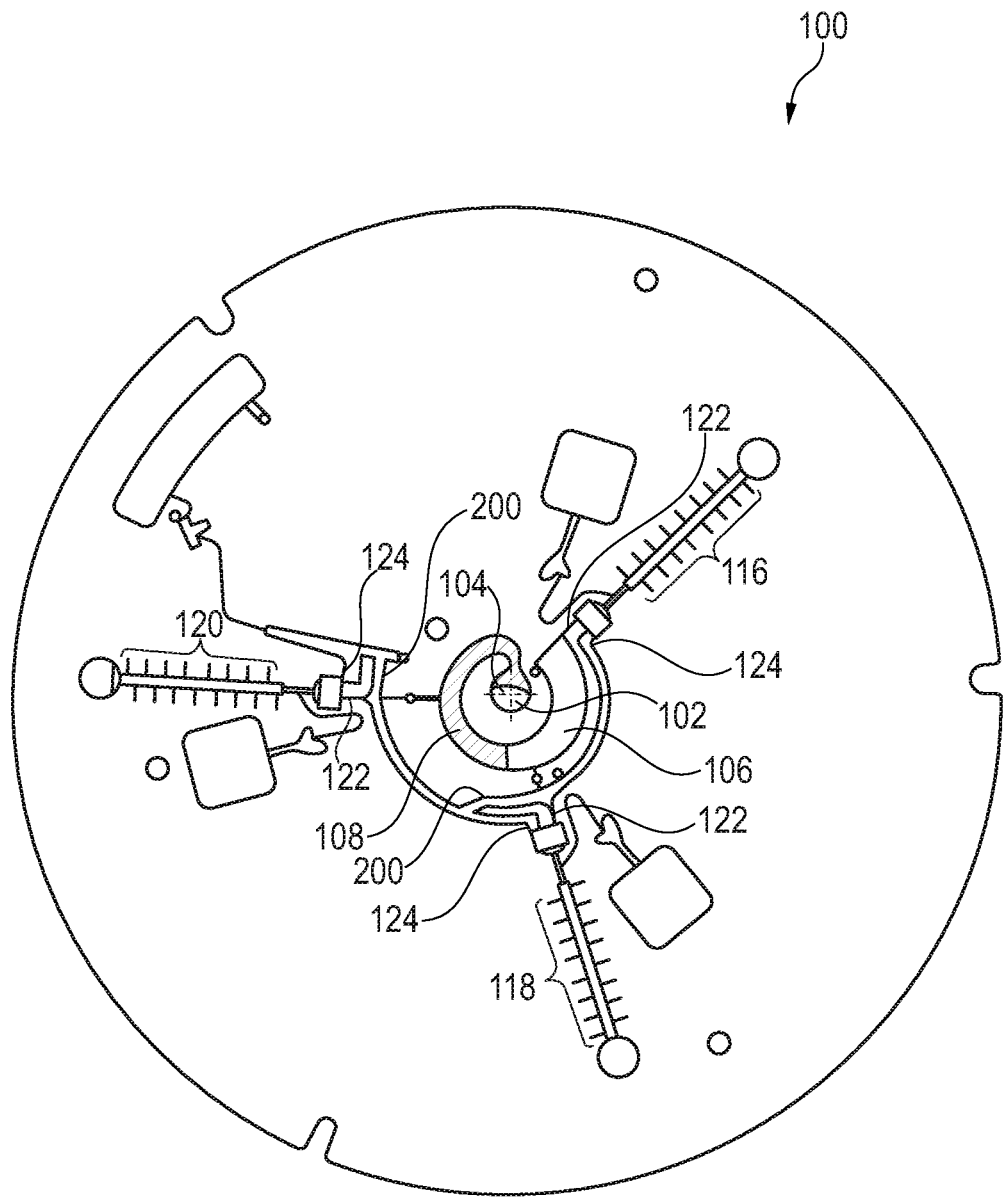
FIG. 2 illustrates a further example of a cartridge.

In FIG. 2 the biological sample 108 has been placed into the sample holding chamber 106 via the cartridge inlet 104. In FIG. 2 the cartridge 100 has not yet been rotated about the rotational axis 102.

Figure 3:
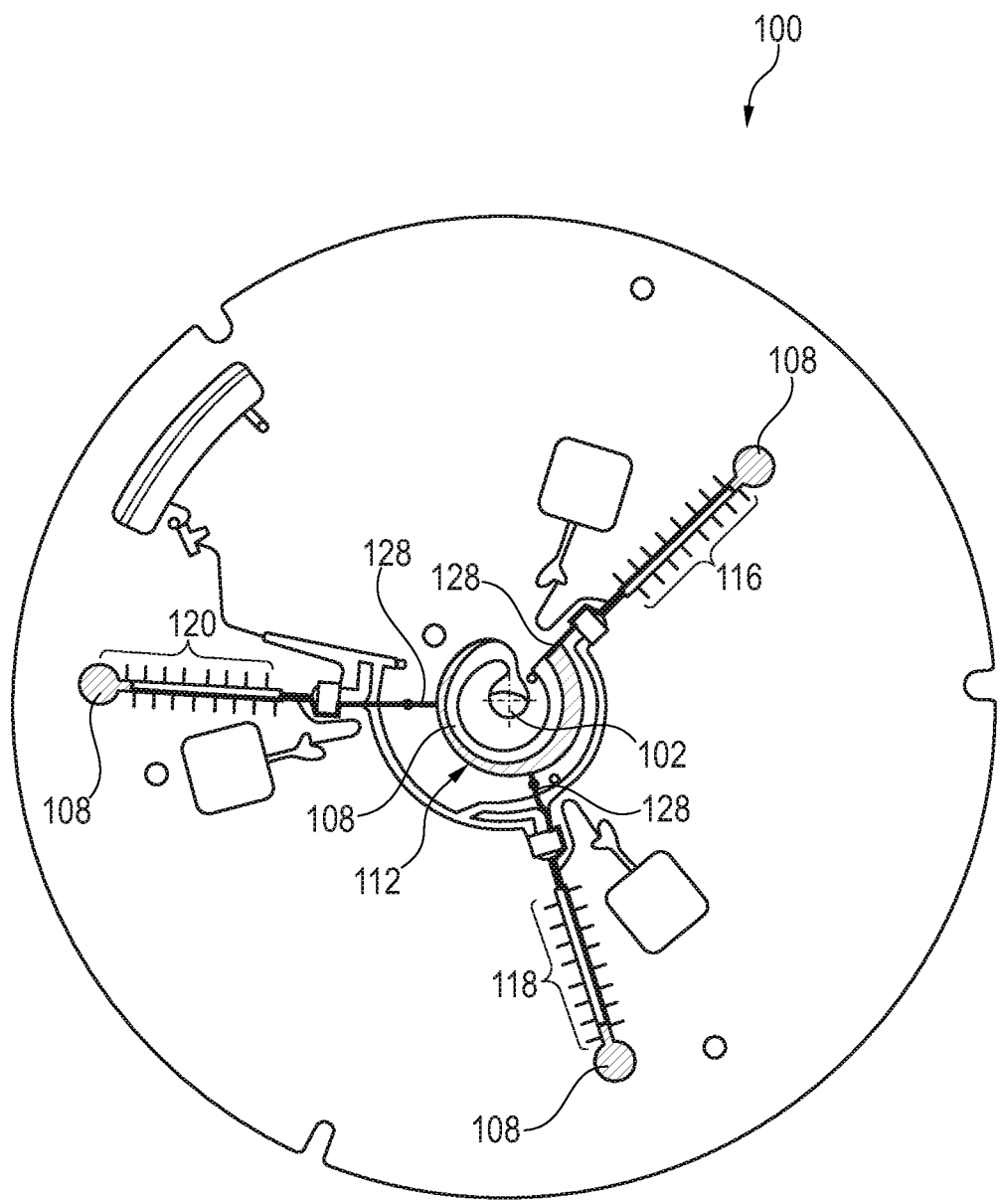
FIG. 3 shows a further view of the cartridge of FIG. 2.

FIG. 3 shows the cartridge 100 shortly after the cartridge 100 has begun to rotate about the rotational axis 102. The centrifugal force forces the biological sample 108 along the furthest edge 112. The three metering chambers 116, 118, 120 begin to be filled via the connecting tubes 128.

Figure 4:
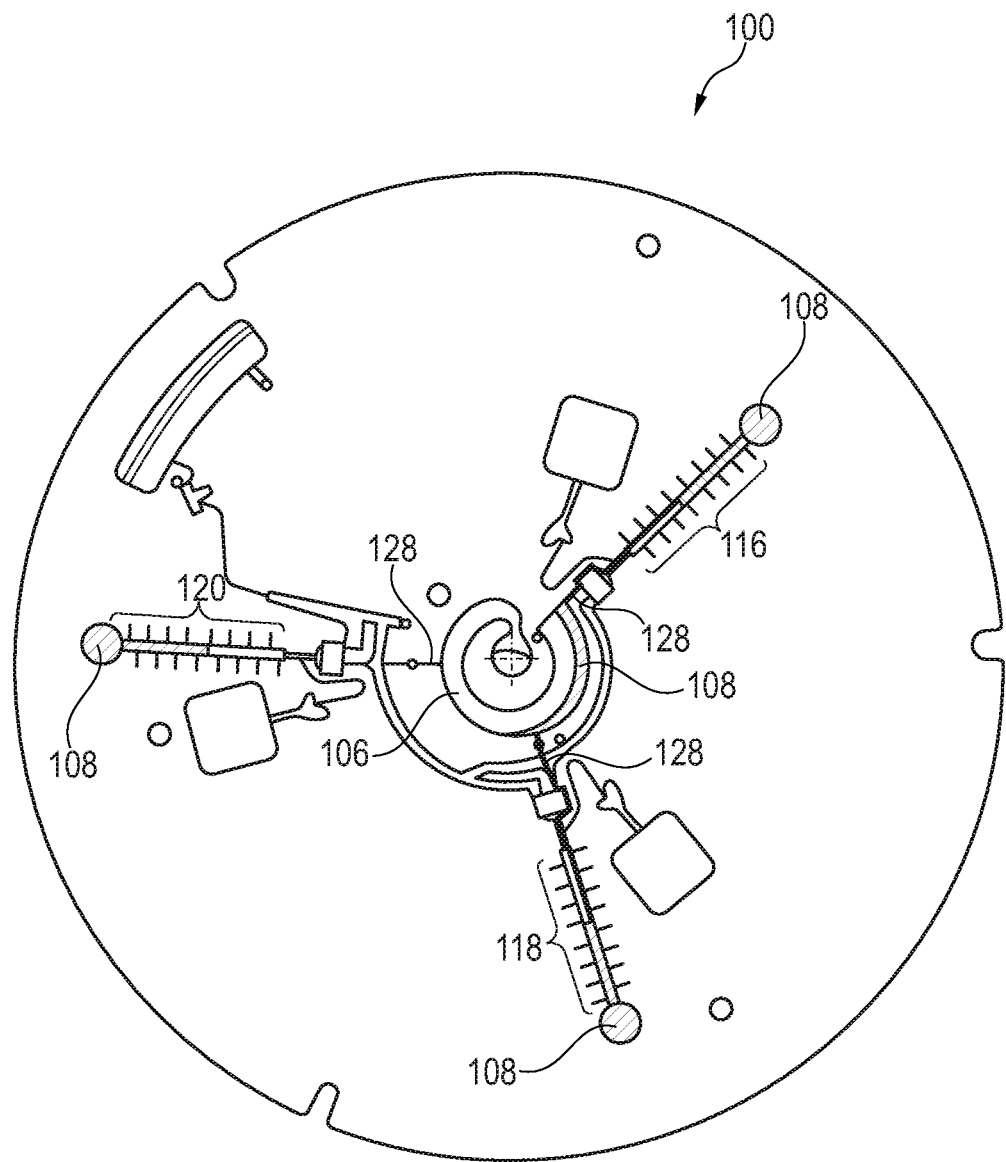
FIG. 4 shows a further view of the cartridge of FIG. 2.

FIG. 4 shows the cartridge 100 after it has been rotated a longer time than is shown in FIG. 3. The amount of the biological sample 108 in the sample holding chamber 106 has been depleted. The amount of the biological sample 108 has decreased to the point that the last metering chamber 120 is no longer being filled with the biological sample 108 by the connecting tube 128. The first metering chamber 116 and the second metering chamber 118 are however still being filled.

Figure 5:
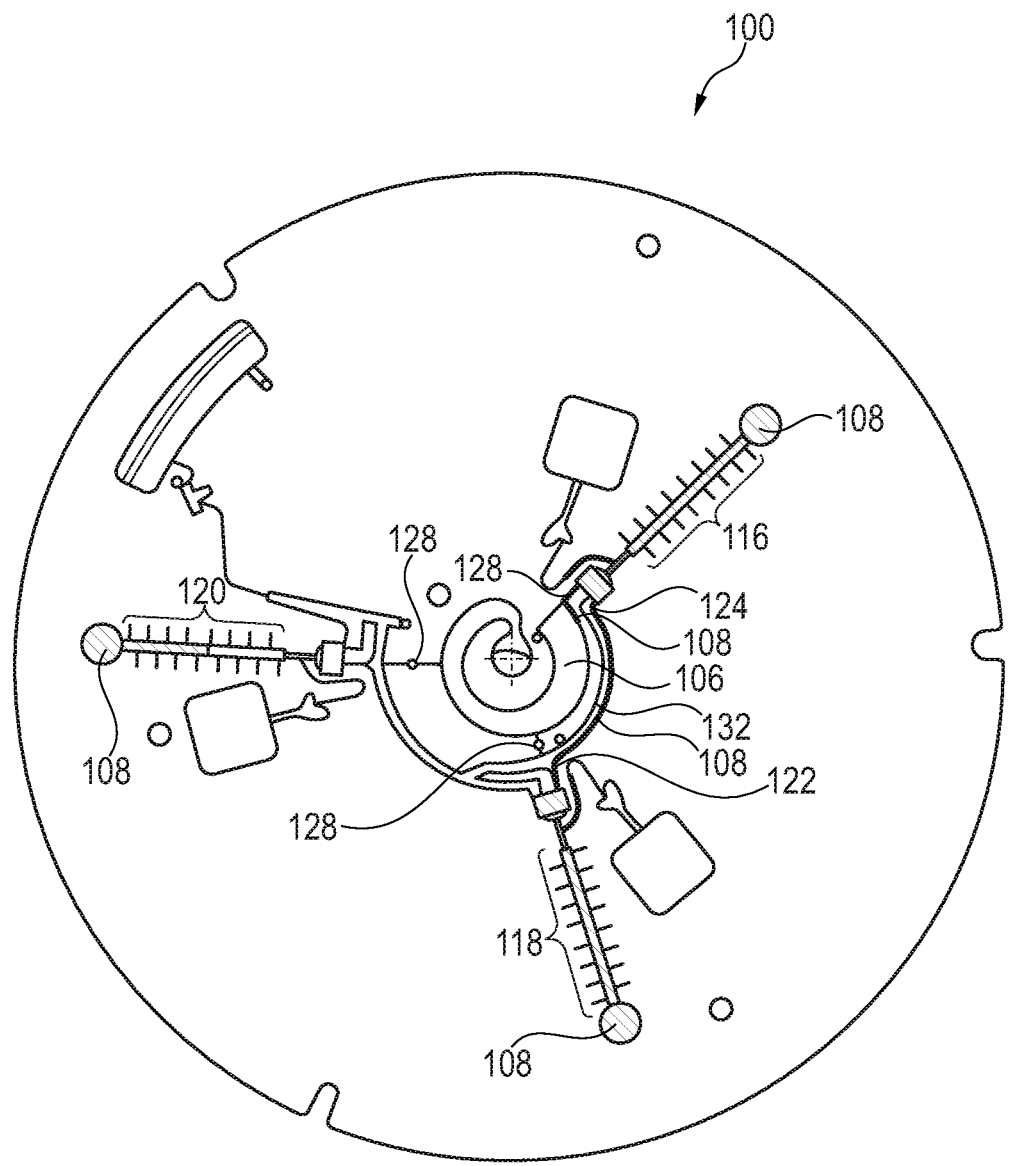
FIG. 5 shows a further view of the cartridge of FIG. 2.

FIG. 5 shows the disc 108 after it has been rotating longer than is shown in FIG. 4. In FIG. 5 the biological sample 108 has almost completely left the sample holding chamber 106. The second metering chamber 118 and the last metering chamber 120 are no longer being filled by the connecting tubes 128. The first metering chamber 116 however at this point has been completely filled. Biological sample 108 is now flowing out of the sample outlet 124 and through the first sample distribution channel 132 to the sample inlet 122 of the second metering chamber 118.

Figure 6:
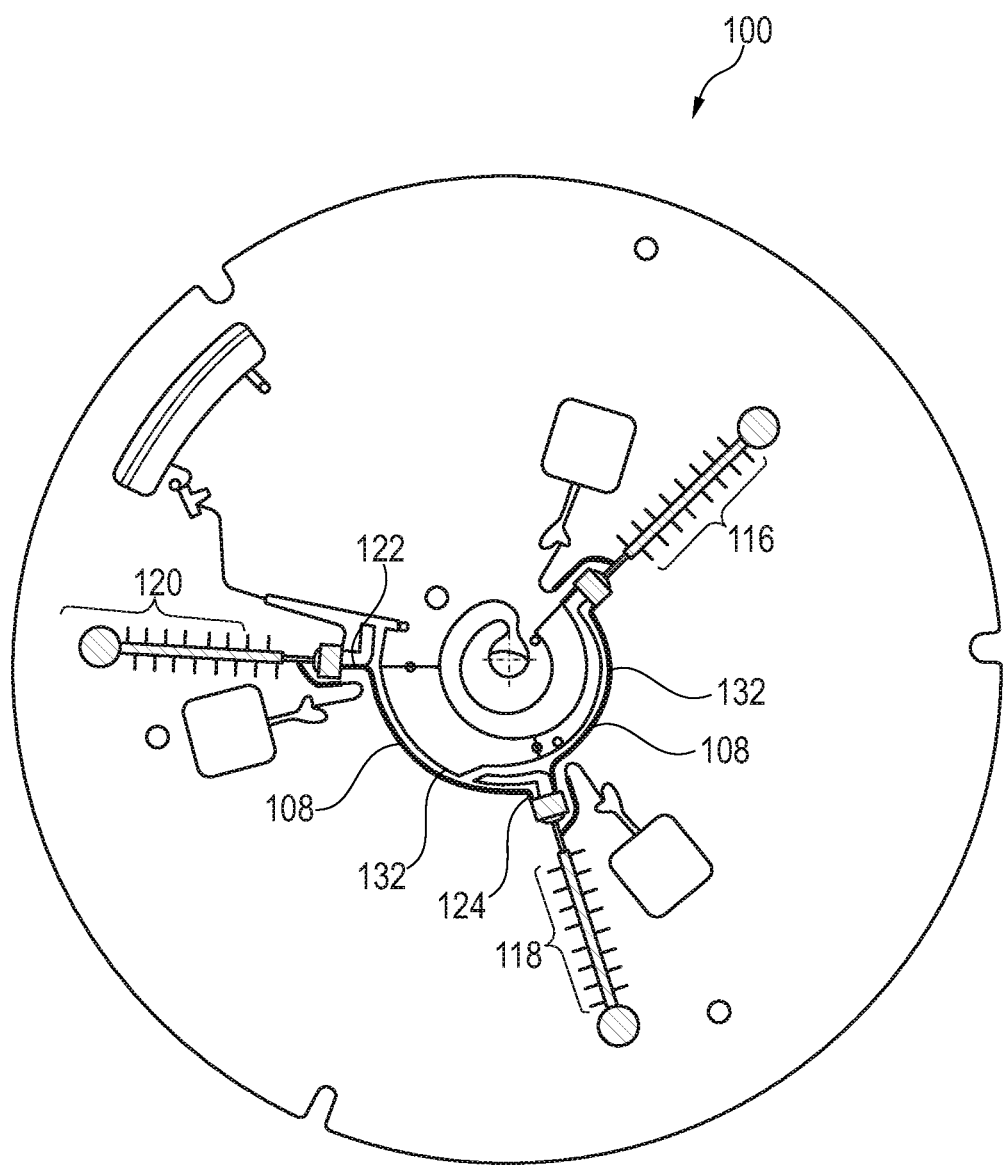
FIG. 6 shows a further view of the cartridge of FIG. 2.

FIG. 6 shows the cartridge 100 after it has been rotating a longer time than is shown in FIG. 5. In FIG. 6 the cartridge 100 is shown at the point when all three metering chambers 116, 118, 120 have been filled. Some biological sample 108 can be shown as travelling through the sample distribution channels 132. After the second metering chamber 118 was filled biological sample began to flow from the sample outlet 124 of the second metering chamber 118 to the sample inlet 122 of the last metering chamber 120.

Figure 7:
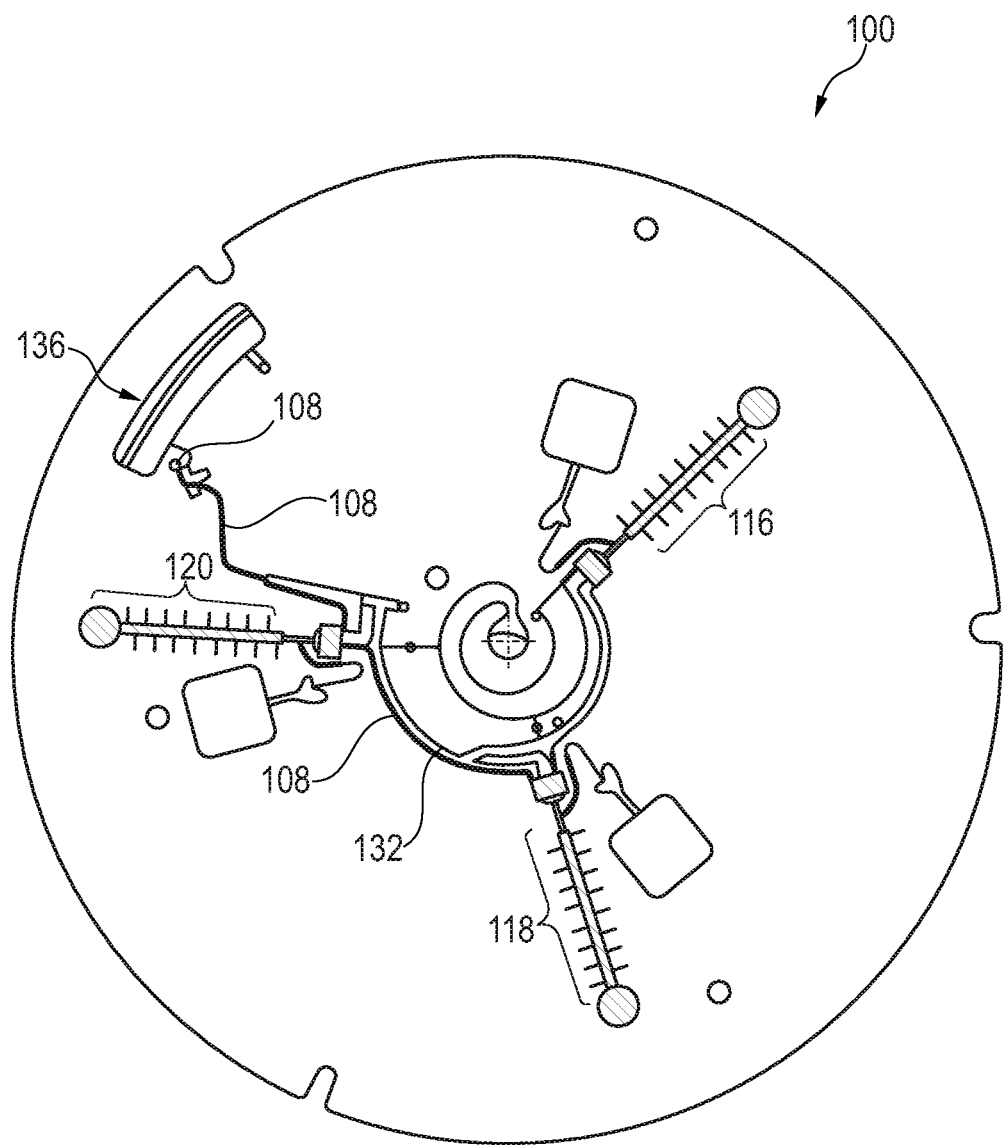
FIG. 7 shows a further view of the cartridge of FIG. 2.

FIG. 7 shows the cartridge 100 after it has been rotated a longer time than is shown in FIG. 6. The cartridge is continued to rotate until excess biological sample 108 is transported to the waste reservoir 136.

Figure 8:
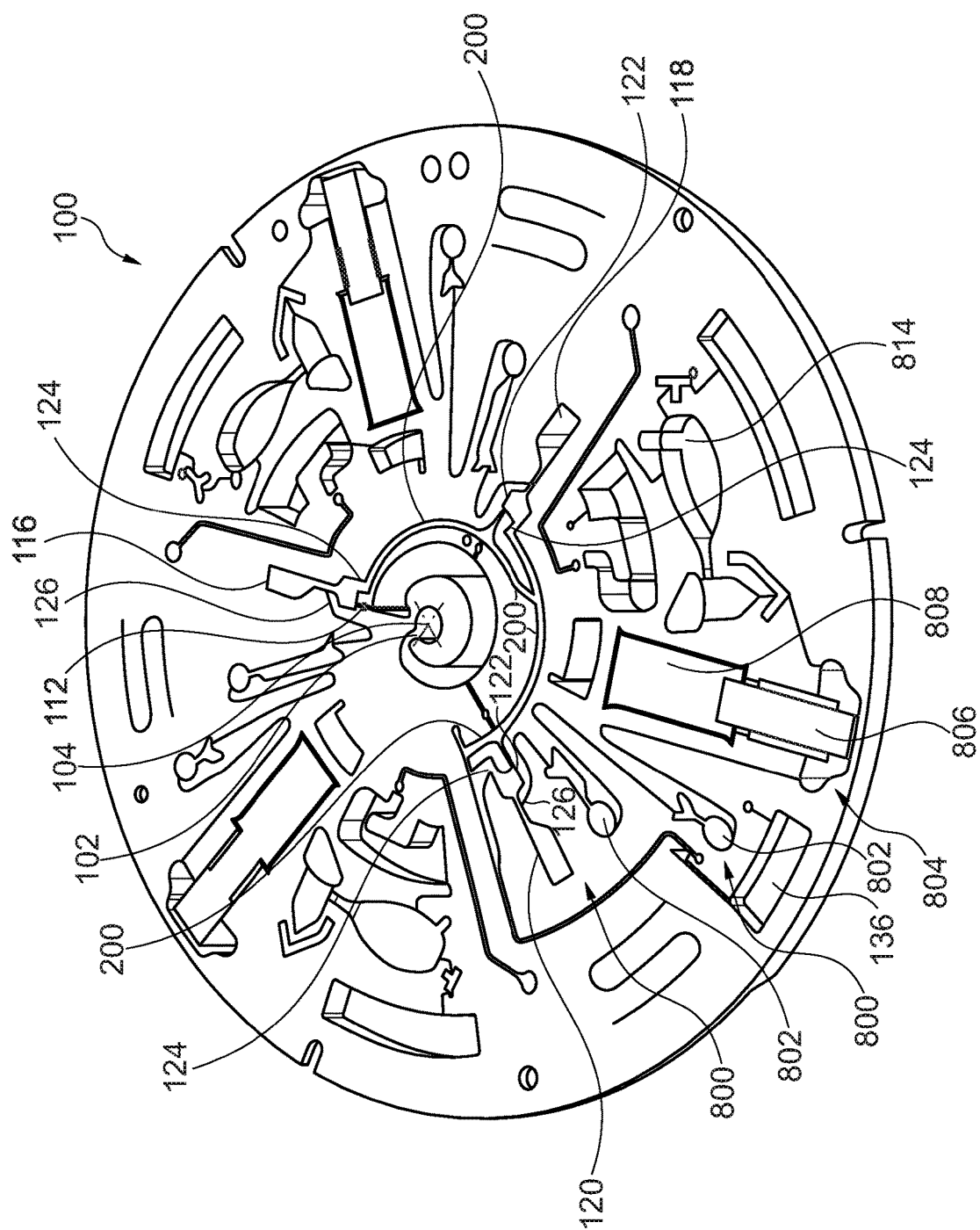
FIG. 8 illustrates a further example of a cartridge.
Figure 9:
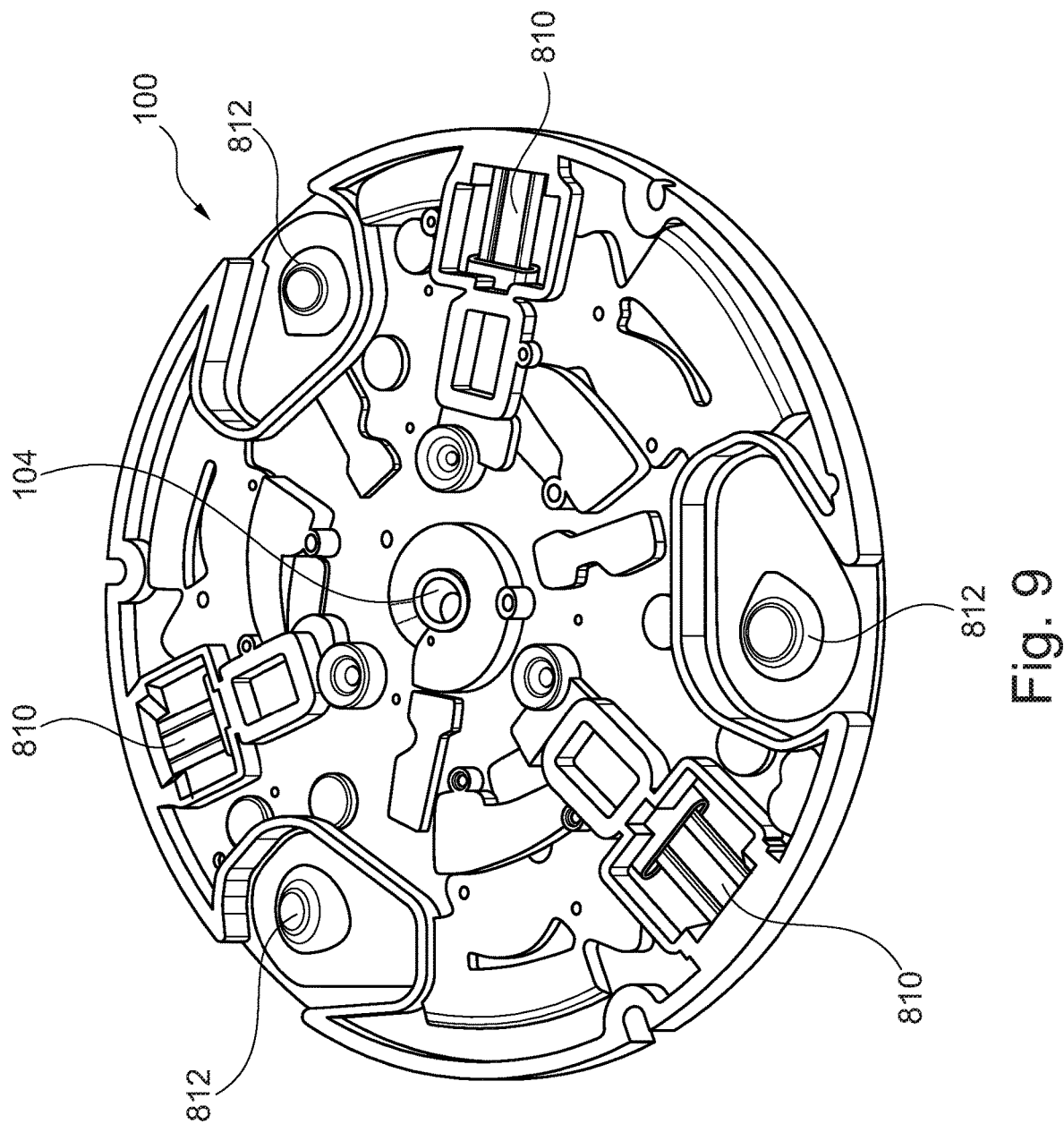
FIG. 9 shows a further view of the cartridge of FIG. 8.

FIG. 8 shows a front view and FIG. 9 shows a back view of a cartridge 100 that is similar to that shown in FIGS. 2-7. In this example the first, second and last metering chambers 116, 118 and 120 are chambers for separating plasma from whole blood. In this example there is a microfluidic structure 800 comprising two reagent chambers 802. The two reagent chambers 802 may be used for combining one or more reagents with blood plasma that exits through the metered output 126. The microfluidic structure 800 is connected to a measurement structure 804. The measurement structure 804 comprises a chromatographic membrane 806 which is in contact with a waste fleece 808. The back side of the cartridge 100 depicted in FIG. 9 shows a detection window 810 which enables a spectrographic instrument to take a measurement on the chromatographic membrane 806. The back side of the cartridge 100 also shows a number of blisters or reservoirs 812 filled with washing buffer. The front of the cartridge 100 shown in FIG. 8 shows a number of aliquoting structures 814 for dispensing the washing buffer multiple times for washing or cleaning the chromatographic membrane 806. The aliquoting structures 814 are similar in function to the structures for dispensing multiple aliquotations of a fluid that are illustrated in international patent application WO 2015/185763.

Figure 10:
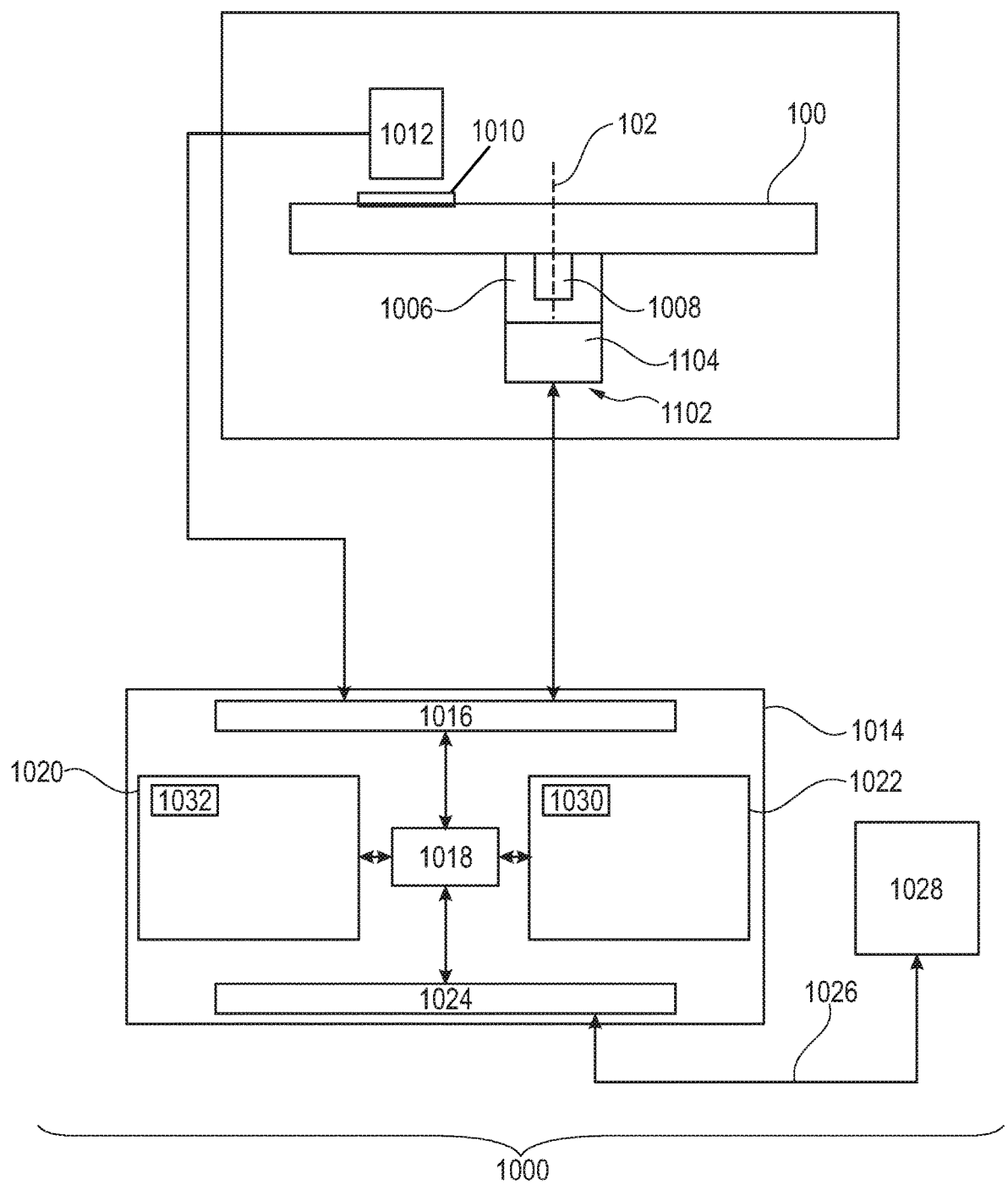
FIG. 10 illustrates an example of an automatic analyzer.

FIG. 10 shows an example of an automatic analyzer 1000. The automatic analyzer 1000 is adapted for receiving a cartridge 100. There is a cartridge spinner 1002 which is operable for rotating the cartridge 100 about the rotational axis 102. The cartridge spinner 1002 has a motor 1004 attached to a gripper 1006 which attaches to a portion of the cartridge 1008. The cartridge 100 is shown further as having a measurement or transparent structure 1010. The cartridge 300 can be rotated such that the measurement structure 1010 goes in front of a measurement system 1012 which can perform for example an optical measurement on the processed biological sample.

The cartridge spinner 1002 and the measurement system 1012 are all shown as being connected to a hardware interface 1016 of a controller 1014. The controller 1014 contains a processor 1018 in communication with the hardware interface 1016, electronic storage 1020, electronic memory 1022, and a network interface 1024. The electronic memory 1030 has machine executable instructions which enable the processor 1018 to control the operation and function of the automatic analyzer 1000. The electronic storage 1020 is shown as containing a measurement 1032 that was acquired when instructions 1030 were executed by the processor 1018. The network interface 1024 enables the processor 1018 to send the measurement 1032 via network interface 1026 to a laboratory information system 1028.

Figure 11:
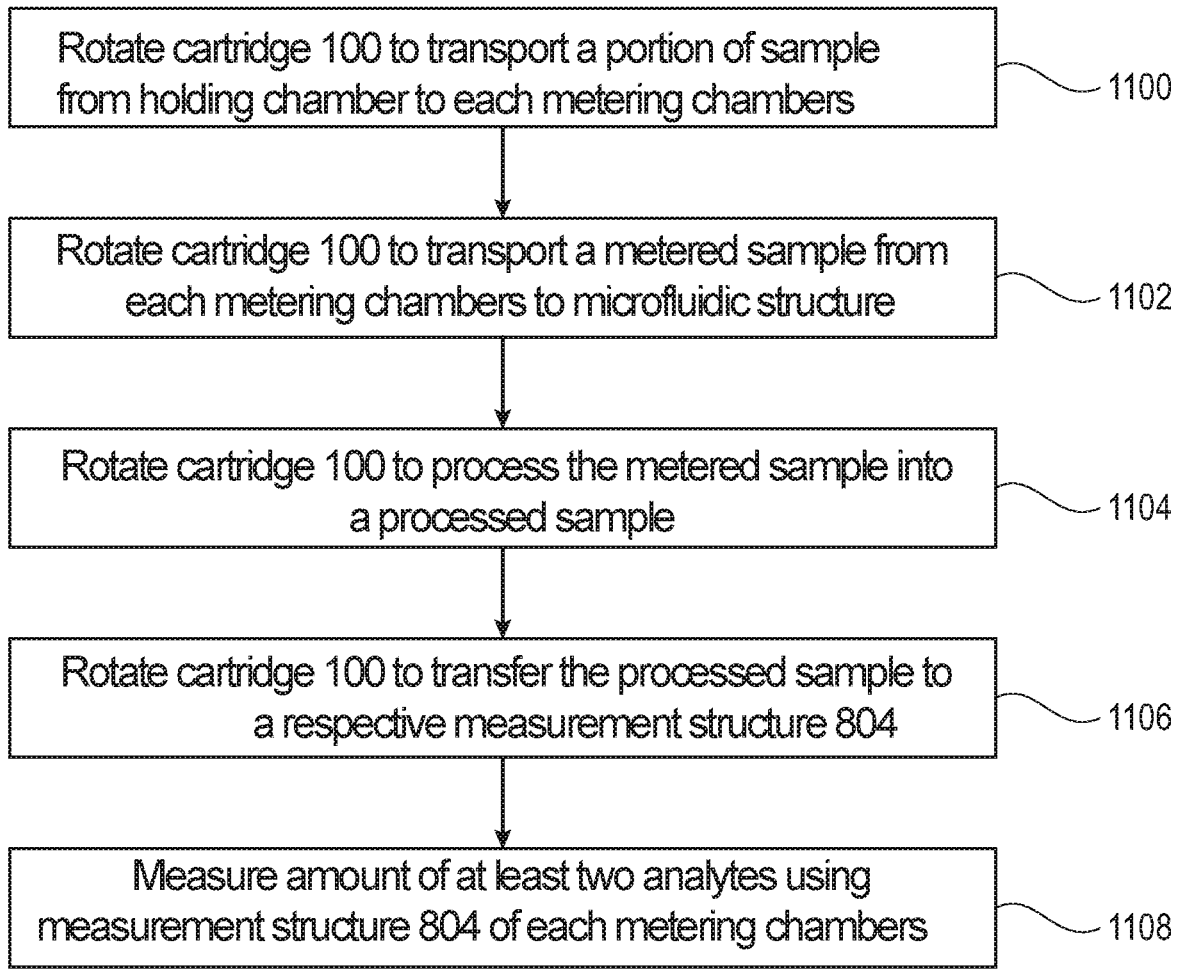
FIG. 11 shows a flow chart which illustrates a method of using the automatic analyzer of FIG. 10.

FIG. 11 shows a flowchart which illustrates a method of operating the automatic analyzer 1000 of FIG. 10. First in step 1100 the cartridge spinner 1002 is controlled to rotate the cartridge 100 about the rotational axis to transport a portion of a biological sample from the sample holding chamber to each of the two or more metering chambers. Rotation of the cartridge causes simultaneous transport of a first part of the portion of the biological sample to each of the two or more metering chambers via the connecting tube for each of the two or more metering chambers. Rotation of the cartridge causes transport of the second part of the portion of the biological sample to each of the two or more metering chambers in serial via the at least one blood distribution channel. Next in step 1102 the cartridge spinner 1002 is further controlled to control the rotation of the cartridge 100 about the rotational axis to transport a metered sample from each of the two or more metering chambers to the microfluidic structure. Next in step 1104 the cartridge spinner 1002 is controlled to rotate the cartridge about the rotational axis to process the metered sample into the processed sample. Next in step 1106 the cartridge spinner 1002 is controlled to rotate the cartridge to transfer the processed sample from the microfluidic structure of each of the two or more metering chambers to its measurement structure 804. Finally in step 1108 the measurement system 1012 is controlled to measure the amount of at least two analytes using the measurement structure 804 of each of the two or more metering chambers.

Further embodiments are disclosed hereafter with reference also made to the figures. For example, a method of determining an amount of at least two analytes in a biological sample 108 using a cartridge 100, wherein the biological sample comprises a fluid, and wherein the cartridge is operable for being spun around a rotational axis 102, is disclosed. The cartridge may comprise:

a cartridge inlet 104 for receiving the biological sample;
  a sample holding chamber 106 fluidically connected to the cartridge inlet;
  two or more metering chambers 116, 118, 120 for receiving a predetermined volume of the biological sample, wherein each of the two or more metering chambers comprises a sample inlet 122, wherein each of the two or more metering chambers comprises a sample outlet 124, wherein each of the two or more metering chambers comprises a metered outlet 126 for dispensing a predetermined volume;
  a connecting tube 128 for each of the two or more metering chambers that fluidically connects the sample inlet with the sample holding chamber;
  at least one sample distribution channel 132, wherein each of the at least one sample distribution channel is connected between the sample outlet of a first selected metering chamber with a sample inlet of a second selected metering chamber, wherein the two or more metering chambers comprises the first selected metering chamber, wherein the two or more metering chambers comprise the second selected metering chamber, wherein the second selected metering chamber is adjacent to the first selected metering chamber;
  a microfluidic structure 800 for each of the two or more metering chambers, wherein the microfluidic structure is connected to the sample outlet, wherein the microfluidic structure is configured for processing the biological sample into a processed sample; and/or
  a measurement structure 804 for each of the two or more metering chambers for enabling measurement of the processed sample to determine a concentration of the analyte in the processed sample, wherein the measurement structure is fluidically connected to the microfluidic structure.

The method may comprise placing the biological sample into the cartridge inlet to at least partially fill the sample holding chamber; rotating 1100 the cartridge about the rotational axis to transport a portion of the sample from the sample holding chamber to each of the two or more metering chambers, wherein rotation of the cartridge causes simultaneous transport of a first part of the portion of the sample to each of the two or more metering chambers via the connecting tube for each of the two or more metering chambers, wherein rotation of the cartridge causes transport of a second part of the portion of the sample to at least one of the two or more metering chambers in serial via the at least one sample distribution channel; controlling 1102 the rotation of the cartridge about the rotational axis to transport a metered biological sample from each of the two or more metering chambers to the microfluidic structure, wherein the metered biological sample has the predetermined volume; controlling 1104 the rotation of the cartridge about the rotational axis to process the metered biological sample into the processed sample; controlling 1106 the rotation of the cartridge to transfer the processed sample from the microfluidic structure to the measurement structure; and measuring 1108 the amount of at least two analytes using the measurement structure of each of the two or more metering chambers and a measurement system.

In another embodiment of the above method, the cartridge inlet can be located closer to the rotational axis than the sample holding chamber, wherein the sample holding chamber is elongated along an elongated path 110, wherein the elongated path at least partially encircles the rotational axis, wherein the sample holding chamber has a furthest edge 112 from the rotational axis, wherein the distance from the furthest edge to the rotational axis increases along the elongated path, wherein the connecting tube for each of the two or more metering chambers is connected to the sample holding chamber at the furthest edge. The fluid can be a multi-component fluid that comprises at least one solid, at least one fluid, and at least one lipid. The biological sample can be a whole blood sample, and wherein the two or more metering chambers can be plasma separation chambers.

In another embodiment, a cartridge 100 for determining an amount of at least two analytes in a biological sample, wherein the cartridge is operable for being spun around a rotational axis 102 is disclosed. The cartridge 100 can comprise:

a cartridge inlet 104 for receiving the biological sample;
  a sample holding chamber 106 fluidically connected to the cartridge inlet;
  two or more metering chambers 116, 118, 120 for the biological sample for receiving a predetermine volume of the biological sample, wherein each of the two or more metering chambers comprises a sample inlet 122, wherein each of the two or more metering chambers comprises a sample outlet 124, wherein each of the two or more metering chambers comprises a metered outlet 126 for dispensing a predetermined volume;
  a connecting tube 128 for each of the two or more metering chambers that fluidically connects the sample inlet with the sample holding chamber;
  at least one sample distribution channel 132, wherein each of the at least one sample distribution chamber is connected between the sample outlet of a first selected metering chamber with a sample inlet of a second selected metering chamber, wherein the two or more metering chambers comprises the first selected metering chamber, wherein the two or more metering chambers comprise the second selected metering chamber, wherein the second selected metering chamber is adjacent to the first selected metering chamber;

a microfluidic structure 800 for each of the two or more metering chambers, wherein the microfluidic structure is connected to the sample outlet, wherein the microfluidic structure is configured for processing sample into a processed sample; and/or a measurement structure 804 for each of the two or more metering chambers for enabling measurement of the processed sample to determine the amount of the analyte in the processed sample, wherein the measurement structure is fluidically connected to the microfluidic structure.

In the above cartridge, the two or more metering chambers may comprise a first filled metering chamber 116 and one or more sequentially filled metering chambers 118, 120, wherein each of the one or more sequentially filled metering chambers comprises a sample bypass channel 200 that fluidically connects the sample inlet with the sample outlet. The at least two analytes each may comprise any one of the following: Troponin T, Troponin I, CKMB, NTproBNP, D-Dimer, Myoglobin, TSH and PCT. The cartridge can be formed from a plastic disk and a cover plate, wherein at least a portion of the sample chamber is visible through the cover plate and/or the plastic disk. The sample holding chamber may be configured for receiving the biological sample with a volume between 30 μL and 500 μL. The cartridge inlet may be located closer to the rotational axis than the sample holding chamber, wherein the sample holding chamber is elongated along an elongated path 110, wherein the elongated path at least partially encircles the rotational axis, wherein the sample holding chamber has a furthest edge 112 from the rotational axis, wherein the distance from the furthest edge to the rotational axis increases along the elongated path, and wherein the connecting tube for each of the two or more metering chambers is connected to the sample holding chamber at the furthest edge. The connecting tube of each of the two or more metering chambers may further connect to one of the at least one sample distribution channel adjacent to the sample inlet. The biological sample may be any one of the following: whole blood, urine, semen, saliva, a stool sample mixed with fluid, blood plasma, blood serum and interstitial fluid.

In still another embodiment, an automatic analyzer 1000 comprising a cartridge 100, wherein the automatic analyzer further comprises a cartridge spinner 1002 for controlling rotation of the cartridge about the rotational axis 102, and wherein the automatic analyzer further comprises a measurement system 1012 for measuring the amount of the at least two analytes using the measurement structure 804 of each of the two or more metering chambers is also disclosed. The automatic analyzer may further comprise a memory 1022 for storing machine executable instructions 1030 and a processor 1018 for controlling the automatic analyzer, wherein execution of the machine executable instructions causes the processor to:

control 1100 the cartridge spinner 1002 to rotate the cartridge 100 about the rotational axis 102 to transport a portion of a biological sample from the sample holding chamber to each of the two or more metering chambers, wherein rotation of the cartridge causes simultaneous transport of a first part of the portion of the biological sample to each of the two or more metering chambers via the connecting tube for each of the two or more metering chambers, wherein rotation of the cartridge causes transport of a second part of the portion of the biological sample to each of the two or more metering chambers in serial via the at least one blood distribution channel;

control 1102 the cartridge spinner to control the rotation of the cartridge about the rotational axis to transport a metered biological sample from each of the two or more plasma separation chambers to the microfluidic structure, wherein the metered biological sample has the predetermined volume;

control 1104 the cartridge spinner to control the rotation of the cartridge about the rotational axis to process the metered biological sample into the processed sample;

control 1106 the cartridge spinner to control the rotation of the cartridge to transfer the processed sample from the microfluidic structure of each of the two or more plasma separation chambers to the measurement structure; and/or measure 1108 the amount of at least two analytes using the measurement structure of each of the two or more plasma separation chambers and a measurement system.

The biological sample can be a whole blood sample, wherein the two or more metering chambers are two or more plasma separation chambers, wherein execution of the machine executable instructions further cause the processor to control the cartridge spinner to control the rotation of the cartridge about the rotational axis to separate blood plasma from the portion of the blood sample in each of the two or more plasma separation chambers by centrifugation.

Having provided reference to specific embodiments, it will be apparent that modifications and variations are possible without departing from the scope of the present disclosure defined in the appended claims. More specifically, although some aspects of the present disclosure may have been identified herein as preferred or particularly advantageous, it is contemplated that the present disclosure is not necessarily limited to these preferred aspects of any specific embodiment.

What is claimed is:

1. A method of determining an amount of at least two analytes in a biological sample using a cartridge, wherein the biological sample comprises a fluid, wherein the cartridge is operable for being spun around a rotational axis, wherein the cartridge comprises:

a cartridge inlet for receiving the biological sample, a sample holding chamber fluidically connected to the cartridge inlet, two or more metering chambers for receiving a predetermined volume of the biological sample, wherein each of the two or more metering chambers comprises a sample inlet, wherein each of the two or more metering chambers comprises a sample outlet, wherein each of the two or more metering chambers comprises a metered outlet for dispensing a predetermined volume, a connecting tube for each of the two or more metering chambers that fluidically connects the sample inlet with the sample holding chamber, at least one sample distribution channel, wherein each of the at least one sample distribution channel connects the sample outlet of a first selected metering chamber with a sample inlet of a second selected metering chamber, wherein the two or more metering chambers comprises the first selected metering chamber, wherein the two or more metering chambers comprise the second selected metering chamber, wherein the second selected metering chamber is adjacent to the first selected metering chamber, a microfluidic structure for each of the two or more metering chambers, wherein the microfluidic structure is connected to the metered outlet, wherein the microfluidic structure is configured for processing the biological sample into a processed sample, and a measurement structure for each of the two or more metering chambers for enabling measurement of the processed sample to determine a concentration of the analyte in the processed sample, wherein the measurement structure is fluidically connected to the microfluidic structure, and wherein the method comprises:

placing the biological sample into the cartridge inlet to at least partially fill the sample holding chamber;

rotating the cartridge about the rotational axis to transport a portion of the sample from the sample holding chamber to each of the two or more metering chambers, wherein rotation of the cartridge causes simultaneous transport of a first part of the portion of the sample to each of the two or more metering chambers via the connecting tube for each of the two or more metering chambers, wherein rotation of the cartridge causes transport of a second part of the portion of the sample to at least one of the two or more metering chambers in serial via the at least one sample distribution channel;

controlling the rotation of the cartridge about the rotational axis to transport a metered biological sample from each of the two or more metering chambers to the microfluidic structure, wherein the metered biological sample has the predetermined volume;

controlling the rotation of the cartridge about the rotational axis to process the metered biological sample into the processed sample;

controlling the rotation of the cartridge to transfer the processed sample from the microfluidic structure to the measurement structure; and measuring the amount of at least two analytes using the measurement structure of each of the two or more metering chambers and a measurement system.

2. The method of claim 1, wherein the cartridge inlet is located closer to the rotational axis than the sample holding chamber, wherein the sample holding chamber is elongated along an elongated path, wherein the elongated path at least partially encircles the rotational axis, wherein the sample holding chamber has a furthest edge from the rotational axis, wherein the distance from the furthest edge to the rotational axis increases along the elongated path, and wherein the connecting tube for each of the two or more metering chambers is connected to the sample holding chamber at the furthest edge.

3. The method of claim 1, wherein the biological sample further comprises at least one solid, and at least one lipid.

4. The method of claim 1, wherein the biological sample is a whole blood sample, and wherein the two or more metering chambers are plasma separation chambers.

5. A cartridge for determining an amount of at least two analytes in a biological sample, wherein the cartridge is operable for being spun around a rotational axis, wherein the cartridge comprises:

a cartridge inlet for receiving the biological sample;
a sample holding chamber fluidically connected to the cartridge inlet;

two or more metering chambers for the biological sample for receiving a predetermine volume of the biological sample, wherein each of the two or more metering chambers comprises a sample inlet, wherein each of the two or more metering chambers comprises a sample outlet, wherein each of the two or more metering chambers comprises a metered outlet for dispensing a predetermined volume;

a connecting tube for each of the two or more metering chambers that fluidically connects the sample inlet with the sample holding chamber;

at least one sample distribution channel, wherein each of the at least one sample distribution chamber connects the sample outlet of a first selected metering chamber with a sample inlet of a second selected metering chamber, wherein the two or more metering chambers comprises the first selected metering chamber, wherein the two or more metering chambers comprise the second selected metering chamber, wherein the second selected metering chamber is adjacent to the first selected metering chamber;

a microfluidic structure for each of the two or more metering chambers, wherein the microfluidic structure is connected to the metered outlet, wherein the microfluidic structure is configured for processing sample into a processed sample; and a measurement structure for each of the two or more metering chambers for enabling measurement of the processed sample to determine the amount of the analyte in the processed sample, wherein the measurement structure is fluidically connected to the microfluidic structure.

6. The cartridge of claim 5, wherein the two or more metering chambers comprise a first filled metering chamber and one or more sequentially filled metering chambers, wherein each of the one or more sequentially filled metering chambers comprises a sample bypass channel, and wherein each sample bypass channel fluidically connects the sample inlet with the sample outlet of a respective one of the one or more sequentially filled metering chambers.

7. The cartridge of claim 5, wherein the at least two analytes each comprise any one of the following: Troponin T, Troponin I, CKMB, NTproBNP, D-Dimer, Myoglobin, TSH and PCT.

8. The cartridge of claim 5, wherein the cartridge is formed from a plastic disk and a cover plate, wherein at least a portion of the sample holding chamber is visible through the cover plate and/or the plastic disk.

9. The cartridge of claim 5, wherein the sample holding chamber is configured for receiving the biological sample with a volume between 30 µL and 500 µL.

10. The cartridge of claim 5, wherein the cartridge inlet is located closer to the rotational axis than the sample holding chamber, wherein the sample holding chamber is elongated along an elongated path, wherein the elongated path at least partially encircles the rotational axis, wherein the sample holding chamber has a furthest edge from the rotational axis, wherein the distance from the furthest edge to the rotational axis increases along the elongated path, and wherein the connecting tube for each of the two or more metering chambers is connected to the sample holding chamber at the furthest edge.

11. The cartridge of claim 5, wherein the connecting tube of each of the two or more metering chambers further connects to one of the at least one sample distribution channel adjacent to the sample inlet.

12. The cartridge of claim 5, wherein the biological sample is any one of the following: whole blood, urine, semen, saliva, a stool sample mixed with fluid, blood plasma, blood serum and interstitial fluid.

13. An automatic analyzer comprising a cartridge according to claim 5, wherein the automatic analyzer further comprises a cartridge spinner for controlling rotation of the cartridge about the rotational axis, and wherein the automatic analyzer further comprises a measurement system for measuring the amount of the at least two analytes using the measurement structure of each of the two or more metering chambers.

14. The automatic analyzer of claim 13, wherein the automatic analyzer further comprises a memory for storing machine executable instructions and a processor for controlling the automatic analyzer, wherein execution of the machine executable instructions causes the processor to:

control the cartridge spinner to rotate the cartridge about the rotational axis to transport a portion of a biological sample from the sample holding chamber to each of the two or more metering chambers, wherein rotation of the cartridge causes simultaneous transport of a first part of the portion of the biological sample to each of the two or more metering chambers via the connecting tube for each of the two or more metering chambers, wherein rotation of the cartridge causes transport of a second part of the portion of the biological sample to each of the two or more metering chambers in serial via the at least one blood distribution channel;

control the cartridge spinner to control the rotation of the cartridge about the rotational axis to transport a metered biological sample from each of the two or more metering chambers to the microfluidic structure, wherein the metered biological sample has the predetermined volume;

control the cartridge spinner to control the rotation of the cartridge about the rotational axis to process the metered biological sample into the processed sample;

control the cartridge spinner to control the rotation of the cartridge to transfer the processed sample from the microfluidic structure of each of the two or more metering chambers to the measurement structure; and measure the amount of at least two analytes using the measurement structure of each of the two or more metering chambers and a measurement system.

15. The automatic analyzer of claim 14, wherein the biological sample is a whole blood sample, wherein the two or more metering chambers are two or more plasma separation chambers, wherein execution of the machine executable instructions further cause the processor to control the cartridge spinner to control the rotation of the cartridge about the rotational axis to separate blood plasma from the portion of the blood sample in each of the two or more plasma separation chambers by centrifugation.

* * * * *